United States Patent [19]
Sirat

[11] Patent Number: 5,892,602
[45] Date of Patent: Apr. 6, 1999

[54] MOBILITY MEASUREMENT USING CONOSCOPIC HOLOGRAPHY

[75] Inventor: Gabriel Y. Sirat, Rehovot, Israel

[73] Assignee: Optiment, Optical Metrology Ltd., Jerusalem, Israel

[21] Appl. No.: 722,277

[22] PCT Filed: Feb. 6, 1996

[86] PCT No.: PCT/FR96/00188

§ 371 Date: Dec. 2, 1996

§ 102(e) Date: Dec. 2, 1996

[87] PCT Pub. No.: WO96/24889

PCT Pub. Date: Aug. 15, 1996

[30] Foreign Application Priority Data

Feb. 10, 1995 [FR] France .................................. 95 01578

[51] Int. Cl.$^6$ .................................. G03H 1/28; H04N 7/18

[52] U.S. Cl. .................................. 359/30; 359/1; 358/105

[58] Field of Search .................................. 359/1, 22, 26, 359/27, 30, 495; 435/6

[56] References Cited

U.S. PATENT DOCUMENTS

| | | | |
|---|---|---|---|
| 4,320,415 | 3/1982 | Jones | 358/105 |
| 4,648,715 | 3/1987 | Ford, Jr. et al. | 356/344 |
| 4,976,504 | 12/1990 | Sirat et al. | 350/3.73 |
| 5,081,540 | 1/1992 | Dufresne et al. | 359/30 |

*Primary Examiner*—Cassandra Spyrou
*Assistant Examiner*—Jared Treas
*Attorney, Agent, or Firm*—Bromberg & Sunstein LLP

[57] ABSTRACT

A method and device for measuring the mobility distribution of particulate elements using incoherent light holography, where the particulate elements are optically labeled. An elementary hologram is formed for each particulate element at a series of periodic moments representing the transfer function as a function of the instantaneous position of that element. The transfer function is modulated by a specified periodic transfer function for labeling each simple hologram and for generating conjugate elementary holograms integrated at each moment for forming a compound velocity hologram containing coded information for each particulate element. Each compound velocity hologram is decoded to obtain specified mobility information.

15 Claims, 9 Drawing Sheets

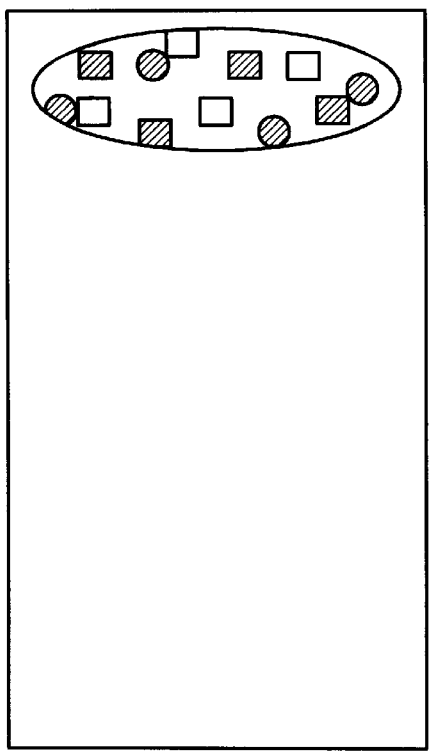
FIG. 1a.
PRIOR ART
(ETM)
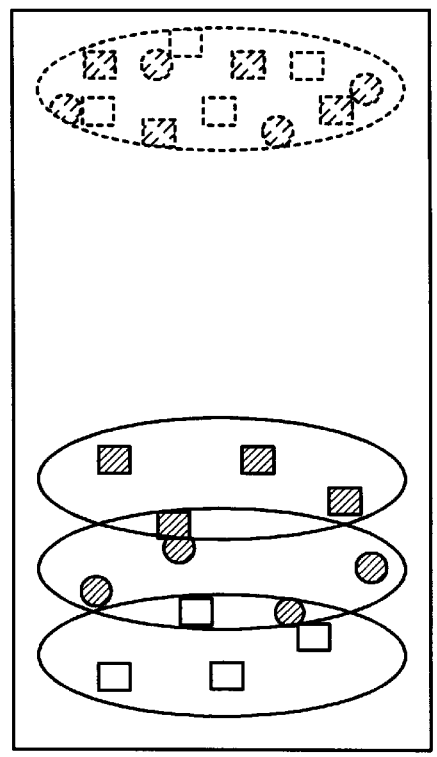
FIG. 1b.
PRIOR ART
(ETM)
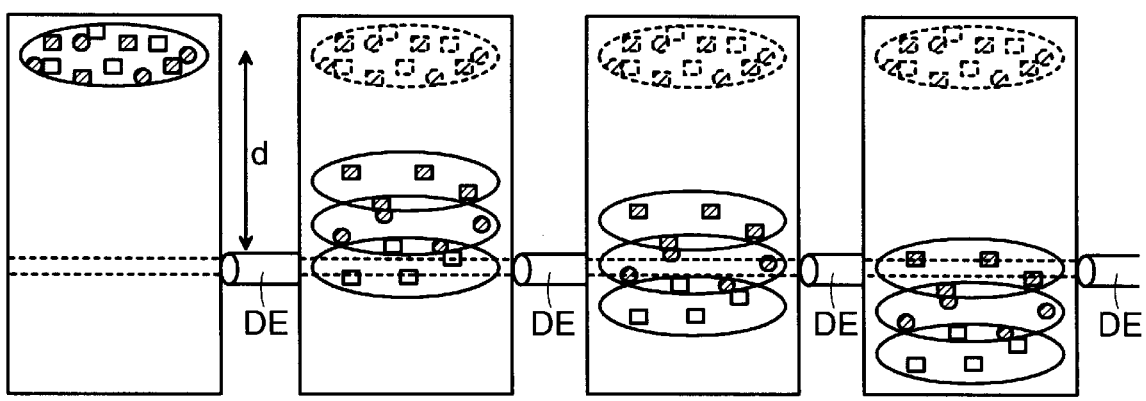
FIG. 1c.
PRIOR ART
(ALTERNATE ETM)
FIG. 1d.
PRIOR ART
(ALTERNATE ETM)
FIG. 1e.
PRIOR ART
(ALTERNATE ETM)
FIG. 1f.
PRIOR ART
(ALTERNATE ETM)

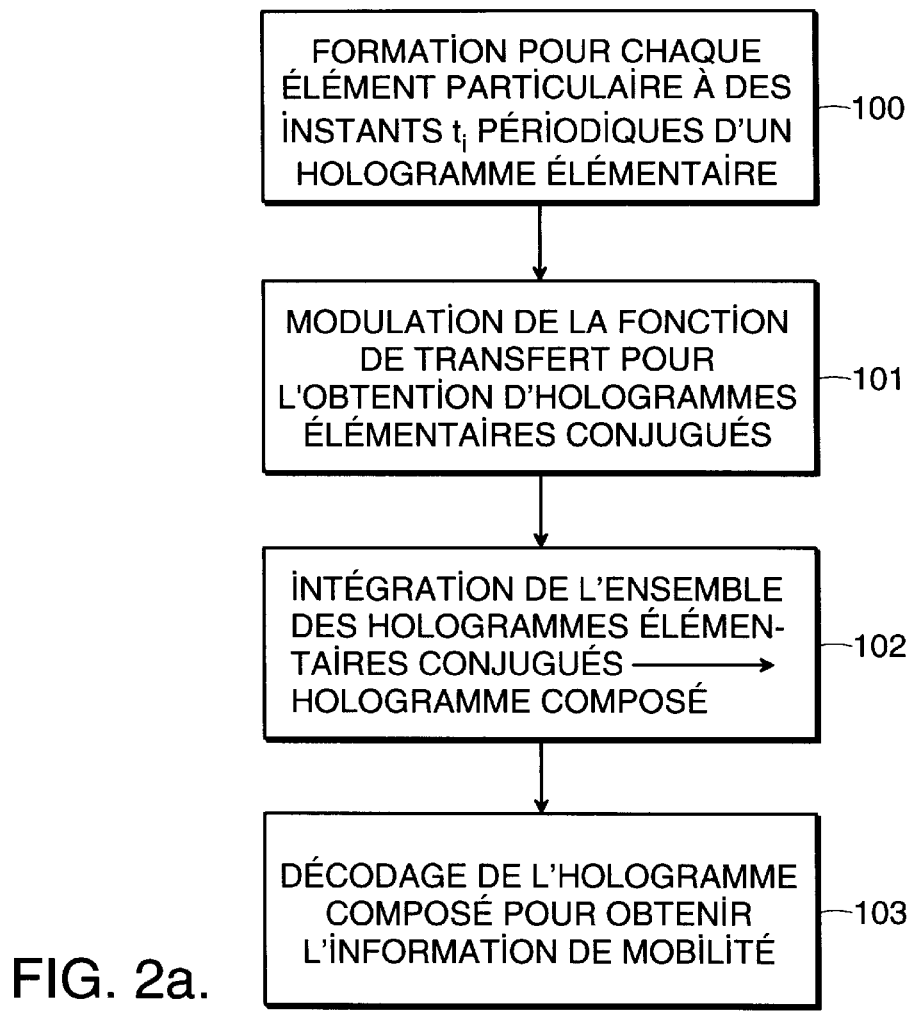
FIG. 2a.
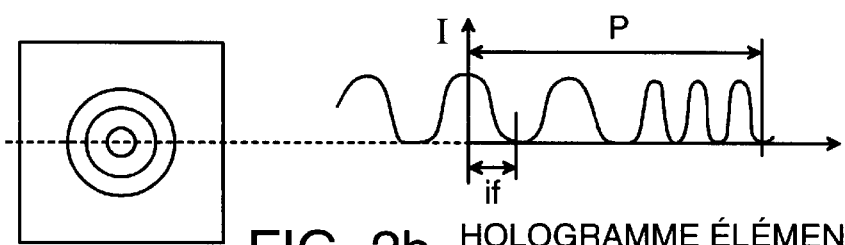
FIG. 2b. HOLOGRAMME ÉLÉMENTAIRE RÉSEAU ZONÉ
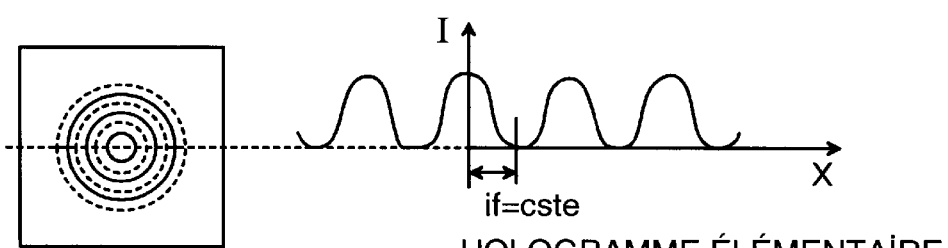
FIG. 2c. HOLOGRAMME ÉLÉMENTAIRE SINUSOÏDALE

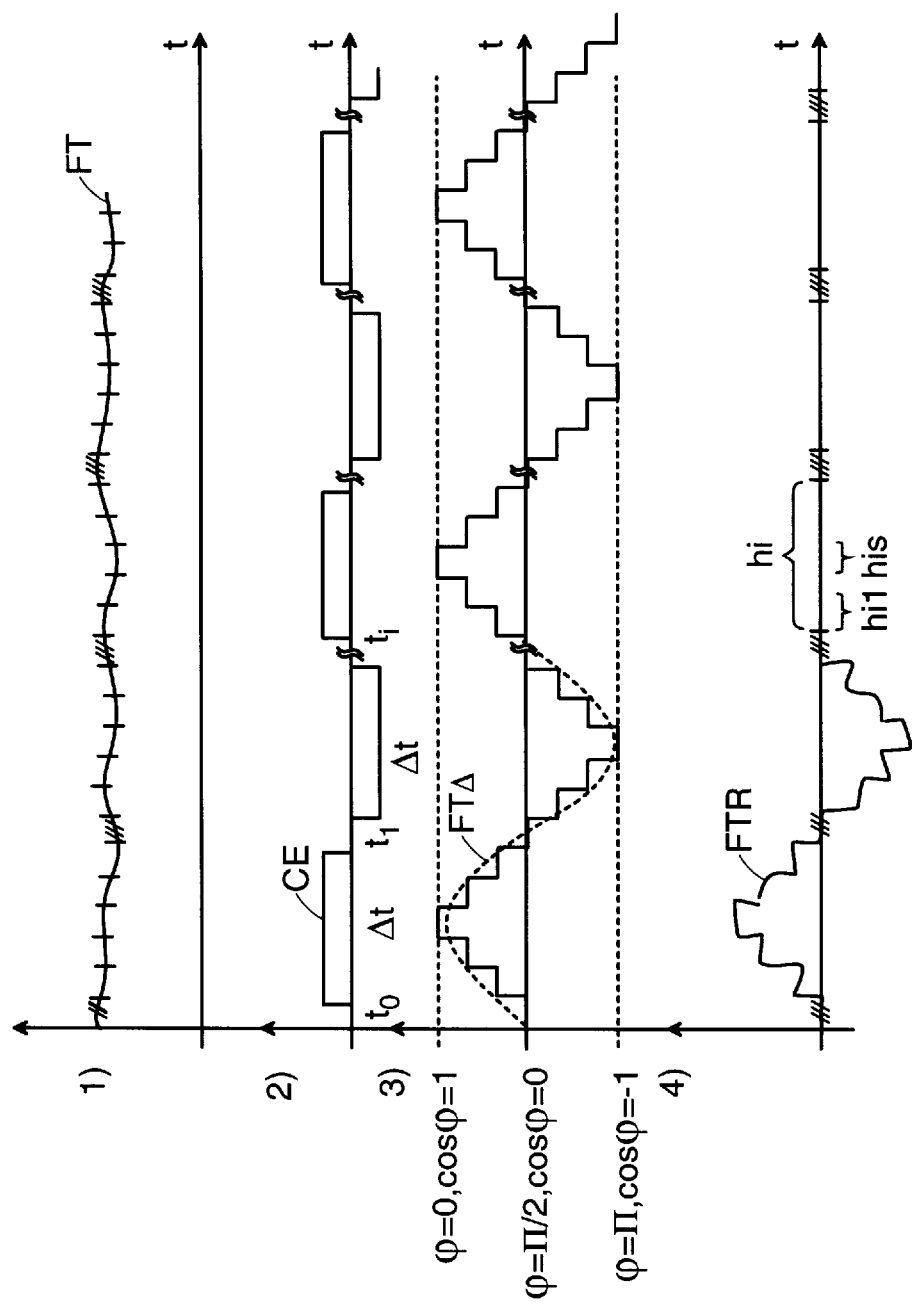

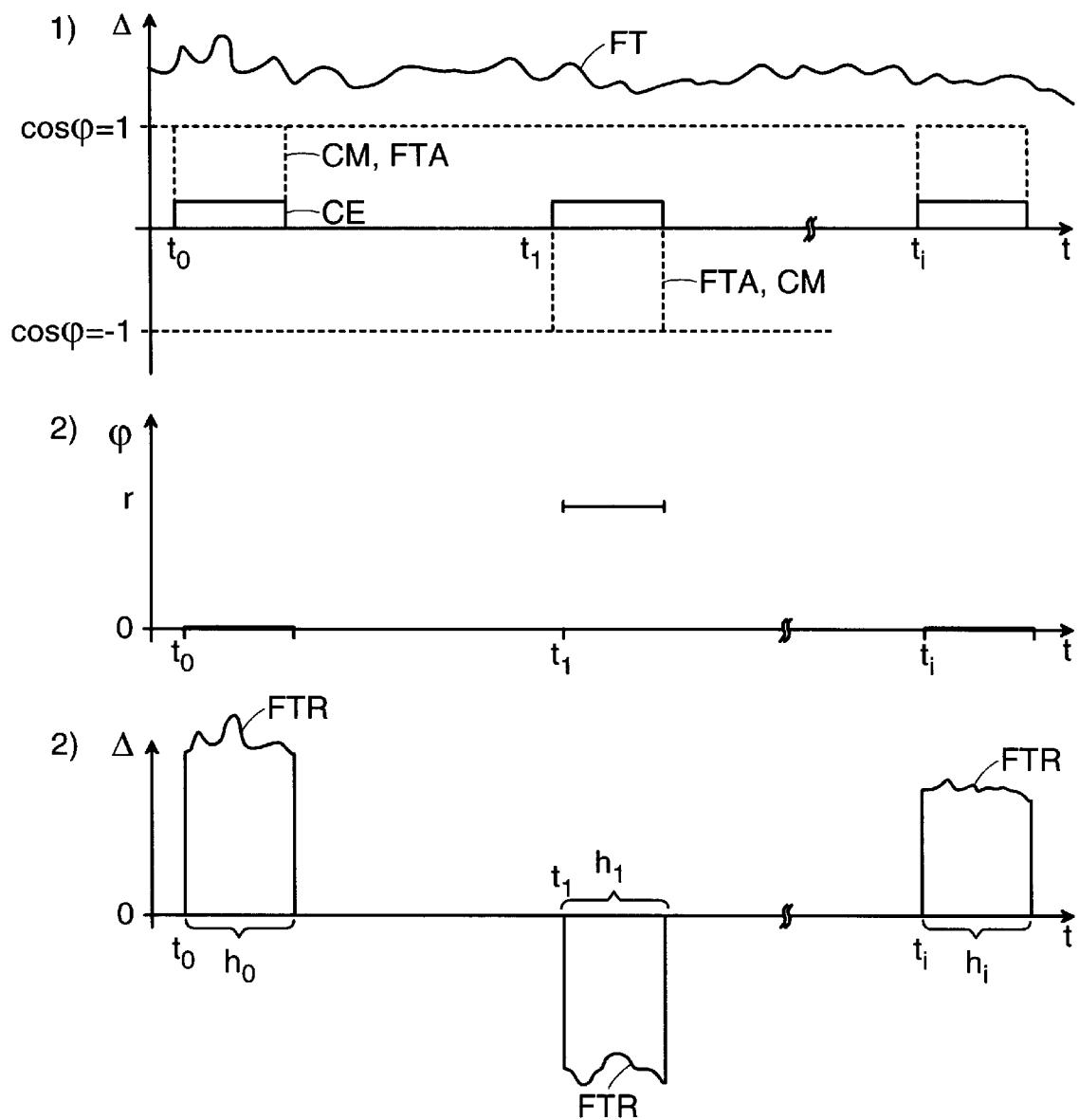
FIG. 3b. MODULATION À DEUX ÉTATS

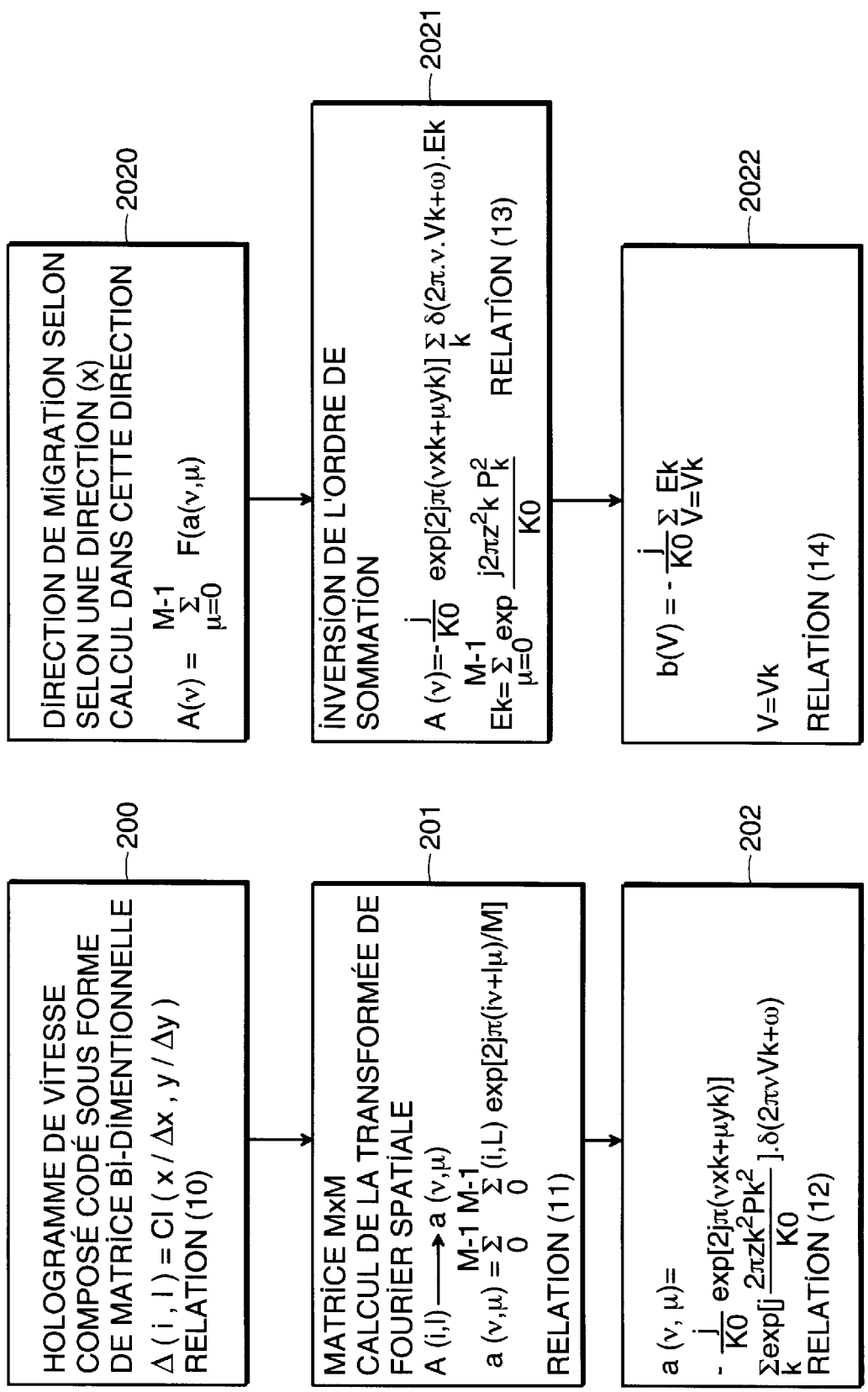

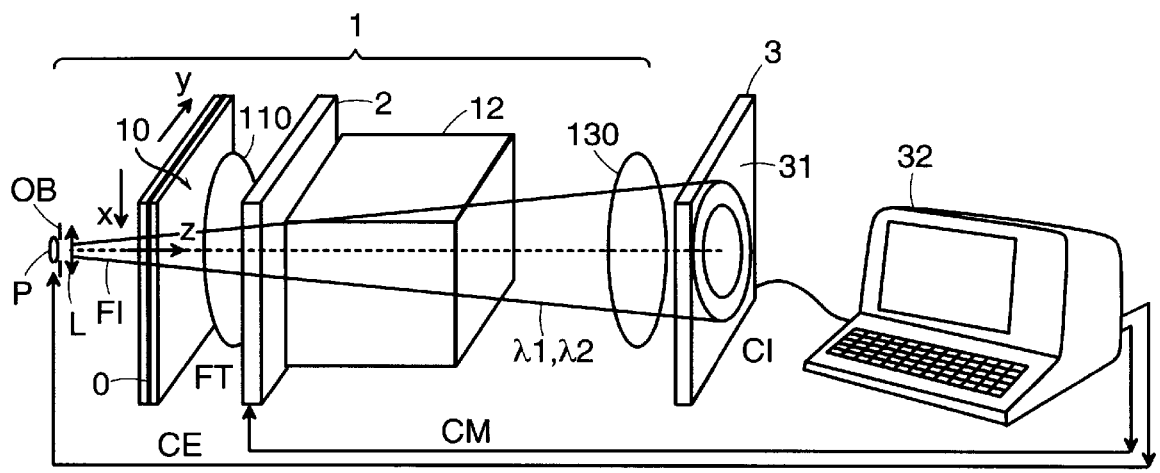
FIG. 6a
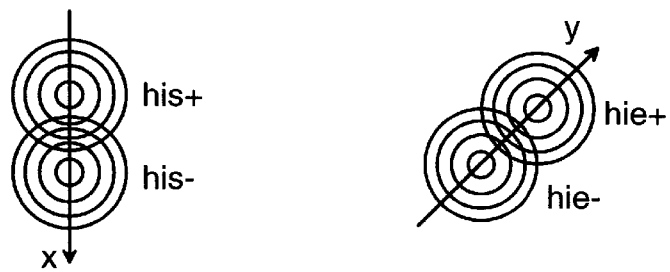
$hi = (his+ + hie+) - (his- + hie-)$
FIG. 6b
| φ | 110 | 130 |
|---|---|---|
|   | π/0 | 0/π |
| λ1 | λ1/2 | λ1 |
| λ2 | λ2 | λ2/2 |
FIG. 6c

MOBILITY MEASUREMENT USING CONOSCOPIC HOLOGRAPHY

FIELD OF THE INVENTION

The invention pertains to a method and a device for measuring the mobility distribution of particulate elements in a medium, using incoherent light holography.

BRIEF SUMMARY OF THE INVENTION

There are currently many technical domains in which being able to discriminate between the particulate elements of a medium is essential. This is particularly true, for example, in the field of fluid mechanics, in chemistry, in biology, or in genetics, where analysis requires the counting and/or the discrimination of molecules, particles, cells, or microspheres.

Studies have already been conducted to allow this type of discrimination or counting of particles.

Among these studies, one can mention the "Elapsed Time Method" (ETM). As represented in FIGS. 1a, and 1b, in such a method, a sample of particles, for instance labeled by using fluorescence, is introduced into a field of forces that act upon the particles. Within a determined period of time, the particles, all of which present different mobility parameters—mobility parameters including a velocity parameter and/or an acceleration parameter—migrated to different positions and are, therefore, physically separated. Particles exhibiting the least inertia are at the farthest from their point of departure, particles exhibiting the greatest inertia are at the closest to their point of departure, and those in the middle are spread among the aforesaid particles. An image of marked particles is recorded, allowing for an evaluation of mobility parameters, either visually or by calculation.

A variation of the precipitate method can be applied by placing a detector at a specified distance from the points of departure of the particles. The detector signal, during the migration of particles, is analyzed as a function of time. As represented in FIGS. 1c to 1f, particles presenting different mobility go through the field of view of detector DE at different times. The signal delivered by the detector represents the particles' mobility as a function of time.

Within this method, time and length of migration necessary to separate two particles of neighboring speed, $V_1$ and $V_2$, at the level of the field of the detector, are given by the relations:

$$t_{12} = 2 \frac{D}{(V_2 - V_1)}$$

$$x_{12} = t_{12} \cdot (V_2 - V_1)/2$$

where D represents an empirical bandwidth parameter which depends on the installation. This bandwidth parameter corresponds to a width, in the direction of migration, over which particles of approximately equal velocity, are spread at a particular point in time. Therefore, there exists a corresponding bandwidth D for a specific installation, and for each velocity value.

The precipitate method, in its two variations, allows measurement of mobility in media in which the intensity of a single particle's signal is below the noise level. Nevertheless, it does not allow individual measurements for each particle, the particles also being discriminated in terms of groups or particle bands presenting parameters of similar mobility, to the value of nearby bands—the signal relative to a band comprising, in fact, the sum of the elementary signals of each particle belonging to the band under consideration.

Consequently, the resolution or the power of discrimination for precipitate methods, as well as for their devices for application, is limited by the width value of the precipitate band. Particularly, in the aforementioned case for the implementation of this method, the particles are presented for a very brief instance in the field of the detector. Under such conditions, it is necessary to produce a highly elevated level of excitation energy, to assure that labeling by using fluorescence can be sufficient for appropriate conditions of detection. The thermal effects generated in these conditions increase the bandwidth parameter, which in itself reduces the system's resolving power.

Another method, consisting of a high speed recording of sequences of images of the medium and of the particles, was proposed with the object of measuring dynamic behavior. Such a method requires the identification of each particle in order to determine its dynamic behavior. While this method does not present the limitations of ETM, for a sufficient degree of certainty in the identification of each particle in each image, it still requires the activation by a significant number of photons. In addition, the use of cameras with fast sequencing capacity introduces a significant noise level in the images, implying a need for an elevated signal level for each particle. Therefore, this method can only be legitimately utilized with particles at high energy, where each particle has a very high level of available light energy. However, this method can be improved by the activation of a variation designated as the Double Pulse Method, DPM. In this variation, two events related to a same particle are recorded at different moments. Each particle is then represented by a doublet of luminous points where the distance between luminous points is proportional to the particle's speed, while the average position of the doublet represents the position of the particle. This technique with this specific variation, while it resolves some of the aforementioned problems, is in fact a specific application of the previously described ETM. Consequently, the problem of ambiguity between neighboring particles with neighboring velocities at a specific moment, limits the application of both this method as well as of its variation DPM to some applications for highly energetic particles.

BRIEF SUMMARY OF THE INVENTION

The object of the present invention is to remedy the limitations mentioned above, by means of a method and a device for measuring the mobility of particulate elements in a medium using incoherent light holography.

An additional object of this invention is the application of a method and a device for measuring mobility distribution of elements that are particularly simple and of a great stability in an industrial environment using corresponding incoherent light holographic devices.

An additional object of the present invention is to provide a method and a device for measuring the mobility distribution of particulate elements which are totally compatible, on the one hand, with classical optical systems and, on the other hand, with incoherent light emission in chemical processes such as fluorescence.

Finally, an additional object of the present invention is the application of a method and a device for measuring the mobility distribution of particulate elements of a medium, which may be integrated with an information processing system performed through micro-computer.

The method for the measurement of mobility distribution of particulate elements of different mobilities, optically labeled, in a medium, by incoherent light holography, which is the object of the present invention, is notable in that it comprises, at least, forming, for each particulate element, an elementary hologram at periodically successive instants, in those instants each elementary hologram being representative of the transfer function, instantaneous position function, of that particulate element in that medium, function of the value of mobility parameters of that particulate element, and modulating this transfer function by means of a periodic specific transfer function where the period equals to or is a multiple of the period of a series of periodic moments, for labeling each elementary hologram, and generating for each particulate element a series of elementary conjugate holograms, corresponding to the transfer functions derived from the modulation value of the specified transfer function. The ensemble of elementary holograms is integrated at each moment by the formation of elementary holograms to form a hologram of compound velocity, containing coded mobility information about each particulate element under that system. Each compound velocity hologram is decoded to obtain information on the mobility of either one or several particulate elements.

The mechanism for measuring the distribution of the mobility of particulate elements of different mobility, optically labeled, in a medium, is outstanding in that it comprises, at least, an incoherent holographic acquisition module of that medium and of each particulate element to form, from a beam emitted or reflected by each of the particulate elements, an elementary hologram at periodic successive moments, each elementary hologram representing during those moments the transfer function of that particulate element in that medium, function of the instant position of that particulate element and of a modulation module of that transfer function by a periodic specific transfer function, wherein the period equals or is a submultiple of the period of periodic successive moments, labeling each elementary hologram and generating, for each particulate element, conjugate successive elementary holograms, corresponding to the transfer functions derived from the value of modulation of the specific transfer function. An integrating module allows at each moment of the formation of elementary holograms, the integration of these elementary holograms into a composite, and the formation of a hologram of composite velocity, that contains the information on the mobility of each coded particulate element.

BRIEF DESCRIPTION OF THE DRAWINGS

A more detailed description of the method and of the device for measuring the mobility distribution of particulate elements, objects of the present invention, will be given in relation to the figures below in which, besides FIG. 1a to 1f, which relate to the prior art, FIG. 2a represents a general flow chart of the steps involved in the method for measuring the mobility distribution of particulate elements, in accordance with the present invention;

FIG. 2b represents an elementary hologram obtained for a particulate element, in incoherent conoscopic holography;

FIG. 2c represents an elementary hologram obtained for a particulate element, in interferometry by incoherent polarization;

FIG. 3a represents, as an illustration, a form of general modulation of the transfer function made up of each particulate element of the medium in accordance with a continuous or approximately continuous periodic law;

FIG. 3b represents a specific embodiment of performing the modulation of the transfer function constituted by each particulate element of the medium, in the case in which two discrete values of modulation are utilized, periodically;

FIG. 5c represents, in a detailed way, a specific flow chart for decoding mobility information, from the coded mobility information contained in the resulting velocity holograms;

FIG. 5d represents a specific embodiment of a processor for decoding the resulting velocity holograms, in the particular case in which the migration of particulate elements occurs in a direction substantially parallel to one of the directions of spatial integration of the two-dimensional detector array;

FIGS. 6a and 6b represent an alternative embodiment of the device in accordance with the invention represented in FIG. 4, the case in which two wavelength components or bands are utilized to constitute the transmitted beam;

FIG. 6c represents, as an example, a specific form of control of the means of modulation, to obtain elementary holograms which differ as a function of wavelengths which differ from the illuminating beam.

DETAILED DESCRIPTION OF SPECIFIC EMBODIMENTS OF THE INVENTION

Figures 3C, 3D:
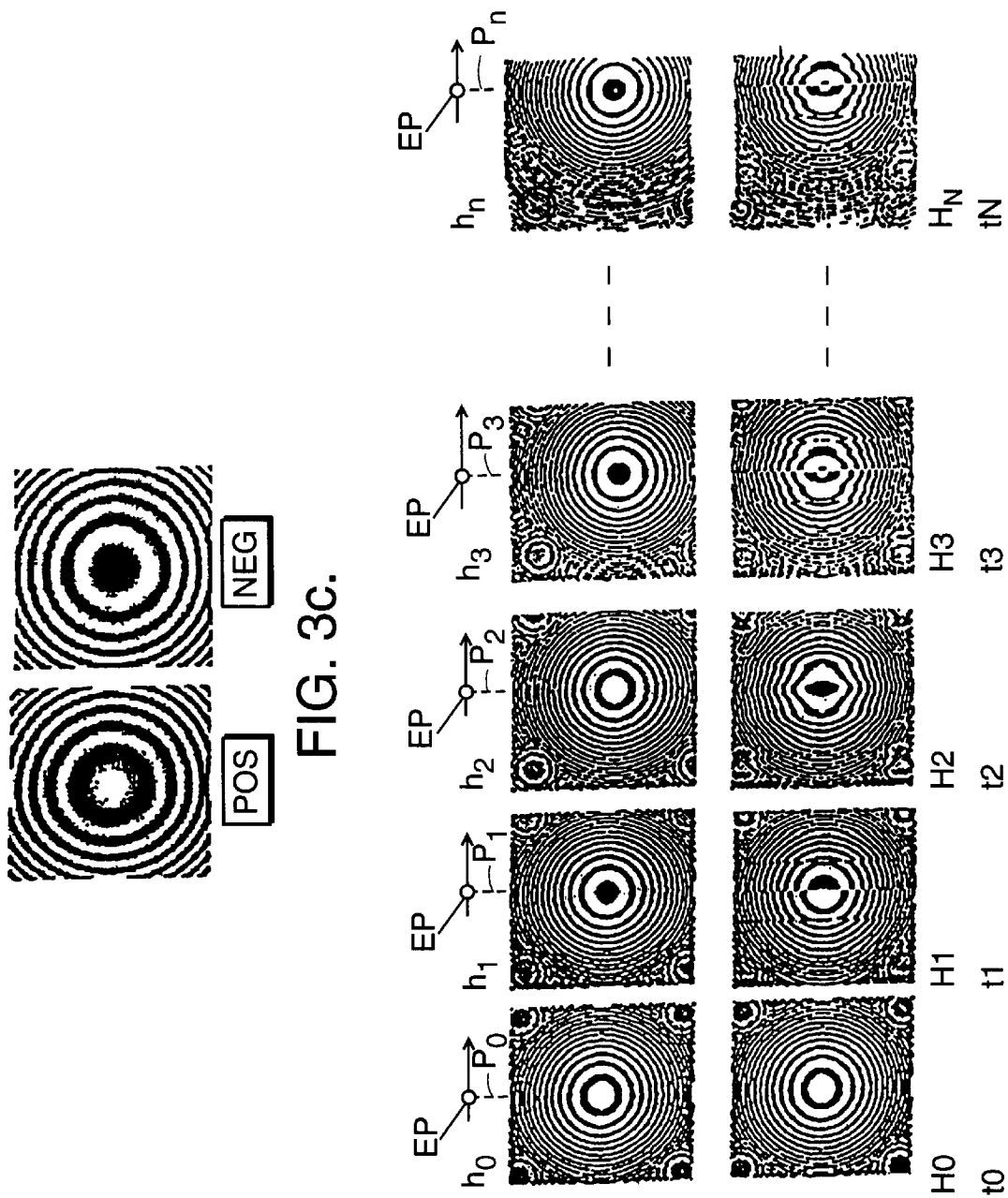
FIG. 3c represents the effect of the modulation on the elementary holograms in the case in which the performed modulation is the one corresponding to the example of FIG. 3b, the elementary holograms obtained in this manner being complementary conjugated elementary holograms.
FIG. 3d represents, as an illustration, the step of integration of the elementary holograms, providing holograms of velocity, which contain the coded mobility information of each elementary particle.

A more detailed description of the method for measuring the mobility distribution of particulate elements in a medium by incoherent light holography will now be given in reference to FIG. 2a.

First of all, it is indicated that the mobile particulate elements can be located in any medium such as a liquid or a gel, especially in the case in which the mobile particulate elements are in suspension in a liquid or a gas, stationary or flowing, and respectively in the case in which the mobile particulate elements are, for instance, contained in a laboratory preparation intended for analysis.

In all cases, it is indicated that the particulate elements are optically labeled, the labeling being either by fluorescence, by coloration, or if the case arises, by a luminous absorption which differs from that of the surrounding environment by each of the particulate elements in order to assure an optical discrimination of the latter. The optical labeling can be done by fluorescein, or by any other fluorescent compound commercially available in the case of cellular mobility or of protein sequencing.

As can be observed in FIG. 2a, it is indicated that the method aspect of the present invention consists of at least one step 100, forming for each particulate element an elementary hologram at periodically successive instants, denoted $t_1$. Each elementary hologram is representative at those instants of the transfer function of that particulate element in the medium under consideration. In this way, each elementary hologram is a function of the instantaneous position of that particulate element in that medium. One understands, of course, that the transfer function defined this way, corresponds to a transmittance in amplitude/-phase, and if the case arises, frequency, corresponding to an emitted beam, reflected or absorbed in incoherent light by the medium and of each of the precipitate particulate elements.

According to a preferred embodiment of this method aspect of the present invention, it is indicated that it equally consists of modulating, in a step denoted 101, this transfer function with a specified periodic transfer function of which the period is equal to, or a multiple of, the period of periodically successive moments to label each elementary hologram and to generate for each particulate element successive conjugate elementary holograms. Then, these successive conjugate elementary holograms correspond to transfer functions shifted by a value of modulation of the specified transfer function, as will be described in the description below.

The step 101 represented in FIG. 2a is then followed by an integration step 102, at each moment of formation $t_1$ of elementary holograms, of the ensemble of these conjugate elementary holograms to form a resulting velocity hologram containing the mobility information of each particulate element coded in this manner.

In fact, one understands that the ensemble of resulting velocity holograms, each one characteristic of the particulate elements, is equally spatially integrated over a domain of spatial integration, corresponding to the zone of sensitivity of a two-dimensional detector array, to generate a composed holographic image, constituting a composite velocity hologram. This composite velocity hologram is particularly remarkable in that it is further possible to decode the mobility information, either of each of the particulate elements, or of the ensemble of the particulate elements.

Finally, the method aspect of the present invention, consists of, in a step 103, decoding each resulting velocity hologram to obtain the mobility information of one or several particulate elements of the precipitate medium. Each decoding step is performed by the topological analysis of the resulting velocity holograms, such as described in the description below.

Conditions for the specific mode of operation that allows for the practice of the method for measuring the mobility distribution of particulate elements in a medium, in accordance with the object of the present invention, will now be given in reference to FIGS. 2b and 2c.

In a general way, it is indicated that the method, aspect of the present invention, is performed by incoherent light holography, the object to be analyzed, that is to say the medium containing the particulate elements, being excited, for instance, by incoherent or coherent light, and in the case of particulate elements labeled by fluorescence, generating an incoherent source placed at the physical position of the particulate element. The rays emitted by this fluorescent source, incident as beam FT in the acceptance cone of the optic placed in front of a conoscope or a polarization interference system, are separated into ordinary and extraordinary beams, by means of a conoscope, or into direct or retarded beams in interferometry by polarization. Any other method of incoherent holography can be utilized.

In the first case, that is the one related to conoscopic analysis, it is indicated that each elementary hologram is comprised of a holographic image of a fringe pattern type, as represented in FIG. 2b, in which each elementary hologram is made up of an image formed by concentric circles of successively maximal and minimal intensity, the distance between the maximum and the minimum, indicated by inter-fringe if, being a function of the distance to the center of the elementary hologram, and decreasing as a function of this distance to a limit value p which corresponds to the spacing of the detector being used. In the case of FIG. 2b, that is of the conoscopic analysis, the fringe pattern presents a classic structure in which the rings are approximately evanescent towards the periphery, the rays of the rings increasing following a square root law.

In the case of an analysis of a transmitted beam FT following the direct and retarded production of beams generated in incoherent light from one of many bi-refringent crystals, each elementary hologram, such as represented in FIG. 2c, is comprised of a holographic image of sinusoidal intensity law, where the light intensity presents maxima and minima from the center of the elementary hologram, and the spacing or inter-fringe if is then constant.

In both cases, it is indicated that the real resolution of each elementary hologram is limited by the spacing p of the detector being utilized.

When the object of analysis is excited by incoherent light, a light source approximately monochromatic can be used, for example, such as a light stemming from a sodium lamp. If the case arises, fluorescent lamps can equally be used.

However, it is indicated in a particularly advantageous way, that in order to make the elementary holograms relative to each particulate element and, of course, to the resulting velocity holograms, the method aspect of the present invention is notable in that it allows, from an incoherent light source, for example fluorescent, to recreate a post-emission coherence by the analysis of the transmitted beam for each constituent ray. The analysis of a beam separates it into two components which are coherent with each other, since they stem from the same generating beam, allowing one to obtain the elementary holograms and holograms of precipitate velocity.

In addition, it might be noted, for this reason, that the use of an incoherent light source, at the emission, is not essential; a coherent light source can be used without any limitation because, whether the initial emission is coherent or not, the method, aspect of the present invention, provides the transmitted beam with a post-emitted coherence, effectively allowing the operationalization of the method.

It is noted that the use of a coherent light source may be indicated in cases where the phenomena to be analyzed, that is to say the mobility parameters of the elementary particles, call for a very high velocity of analysis and of treatment, such as for flows, and also where a density of luminous power is necessary in order to assure the illumination of the medium and the particulate elements, to allow for the operationalization of the method. The luminous power density is a function of the medium being used and of the particles contained in that medium.

In general, it might be noted that the formation steps 100 for each particulate element at periodic instants $t_i$ of an elementary hologram and of modulation 101 of the transfer function modulation for obtaining conjugate elementary holograms, while they are represented as successive in FIG. 2a, they are performed simultaneously. In fact, it is to be understood that the formation step 100 of an elementary hologram at each instant $t_i$ results from either analysis by means of a conoscope of the transmitted beam, or analysis of that same transmitted beam through an interference system by polarization, such as was previously described. Consequently, modulation step 101 is advantageously performed approximately simultaneously to the formation of elementary holograms, insofar as this modulation step intervenes simultaneously to the creation of ordinary and extraordinary beams by means of a conoscope, or in the case of direct and retarded beams by a polarizing interference system. As represented in FIG. 3a, in an embodiment that is particularly advantageous but non-limiting, the modulation step 101 can consist of introducing, over the emitted or reflected beam FT transmitted by the medium at the time of the creation of the beams ordinary and extraordinary or respectively direct and retarded, an auxiliary transfer function FTA, continuously variable in time, and of controlling the variation of time of this auxiliary transfer function in accordance with a series of values of periodically auxiliary transfer functions. Referring to FIG. 3a, there is represented, as a nonlimiting example at point 1, the time plot of the amplitude of the transfer function FT before modulation for a determined elementary particle, that is to say, of the amplitude value of the transmittance. The amplitude evolution of this transfer function FT is totally arbitrary. Of course, one understands that a specific dephasing value, not represented in FIG. 3a corresponds equally to each amplitude value of the transfer function FT.

At point 2 of the same FIG. 3a, a periodic control signal is represented, denoted CE, which allows the illumination of the medium and of the elementary particles contained in it at illuminating instants $t_0$, $t_1$, where the double integral sign over the time axis corresponds to an arbitrarily determined time value.

At point 3 of FIG. 3a, the variation with time of the auxiliary transfer function is represented, denoted FTA, in accordance with an approximately continuous variation, for example, of a sinusoidal type of variation. It is understood, when observing point 3 of FIG. 3a, that the auxiliary transfer function FTA can be realized by controlling a continuous dephasing brought into the trajectory of the transmitted beam through the analyzed body. In such case, and in a non-limiting way, it is indicated that this control of continuous dephasing can be performed by means of a cell of nematic liquid crystals controlled by a specific electric signal, where the signal is sinusoidal and of the same frequency as the dephasing variation frequency introduced on the transfer function FT of each elementary particle. The auxiliary transfer function FTA is represented by a dashed plot in FIG. 3a.

It is understood, of course, that any continuous function, such as the sinusoidal function representing the variation of the auxiliary transfer function FTA, can also be approximated by a series of sampled values, such as represented as a continuous line in plot 3 in FIG. 3a, where the control signal CM of the nematic liquid crystals cell is used for this purpose in order to introduce the corresponding dephasing control this one being a corresponding sampled signal.

At point 4 of FIG. 3a, the resulting transfer function, denoted FTR, is represented. In terms of its amplitude as a function of time, this function represents the product of the initial transfer function FT, and of the auxiliary transfer function FTA resulting from the phase shift introduced by phase modulation by the aforementioned auxiliary transfer function.

It is understood, in this manner, that the generated successive elementary holograms, relative to the same sampled elementary particle, constitute conjugated holographic images, that is to say holographic images for which a well determined phase relation was obtained.

In the non-limiting case of FIG. 3a, it is understood that when, for example, the auxiliary transfer function FTA is sampled, it is possible to obtain, for an instant of illumination $t_i$, an elementary hologram $h_i$, which is thus comprised of a series of sampled elementary holograms, denoted $h_{is}$, each one obtained at the sampling period of the auxiliary transfer function FTA.

An alternate embodiment of the modulation described in FIG. 3a will be now described in reference to FIG. 3b in the case where, during the interval of time of illumination $\Delta t$ of each instant of illumination $t_i$, the auxiliary transfer function FTA is constant and equal, for example, to +1 or to −1, a phase shift of 0 or $\pi$ being introduced on the transfer function of each elementary particle at aforementioned instants of illumination $t_i$.

At point 1 of FIG. 3b, the amplitude diagram as a function of time of the transfer function FT for each particulate element is represented, as well as, in dashes, the auxiliary transfer function FTA, this function being equal to +1 or −1 in amplitude, that is to say $\phi=0$ or $\pi$, dephasing being introduced over the trajectory of the beam transmitted at instants of illumination by the control signal CE, at the instants $t_i$ previously cited, and also represented at point 2 of FIG. 3b. The product of the transfer function FT and of the auxiliary transfer function FTA, in amplitude, is represented at point 3 of FIG. 3b, and, of course, one finds again a functioning principle analogous to that of FIG. 3a, each elementary hologram $h_i$ being comprised, in the case of the embodiment of FIG. 3b, by only one elementary hologram.

Finally, FIG. 3c represents two elementary holograms obtained by the type of modulation described before in relation with FIG. 3b, that is at the time of the introduction of a dephasing of 0, $\pi$ to two successive instants of illumination, $t_i$, $t_{i+1}$. It corroborates that, for example for holograms comprised of fringe patterns, also known as a Gabor zone, these holograms are successively positive and negative respectively, the conjugate elementary holograms being then complementary holographic images, such as observed in FIG. 3c.

The elementary holograms having been obtained in the way already described, the integration step of these elementary holograms allows one thus to obtain the resulting velocity holograms such as it was previously mentioned in the description, the integration step being now described in reference to FIG. 3d.

In the aformentioned FIG. 3d, a particulate element EP which occupies successive positions $P_0$, $P_1$, $P_2$, $P_3$ ... $P_N$ is represented.

For position $P_0$ of the particulate element EP, with the implementation of the method of the invention such as previously described, one obtains an elementary hologram ho such as represented in FIG. 3d. For each successive position $P_1$, $P_2$, $P_3$ to PN that follow, one obtains the elementary holograms $h_1$, $h_2$, $h_3$, ... $h_N$, as well.

One corroborates that, of course, the center of the fringe pattern or of the hologram of sinusoidal law shifts in the direction of motion of the particulate element EP symbolized by the arrow, and that, of course, in the case of the modulation represented in FIG. 3b, each elementary hologram is a successively complementary holographic image.

In accordance with an aspect of the present invention, the integration process, therefore, allows one, as represented in FIG. 3d, to obtain the successive resulting velocity holograms, denoted $H_0$, $H_1$, $H_2$, $H_3$, to $H_N$, each aformentioned resulting velocity hologram being obtained at instants of illumination $t_0$, $t_1$, $t_2$, $t_3$ to $t_N$, and containing the mobility information of each particulate element coded in this way, as will be described below.

In this way, each resulting velocity hologram can be expressed in terms of the relation (1):

$$H_N = h_0 + h_1 + \ldots + h_N$$

One corroborates that, other than the resulting velocity hologram $H_0$ equal to the elementary hologram $h_0$ due to the fact that the time origin is arbitrarily taken from the To position of the particulate element, each resulting velocity hologram is equal to the sum of the previous elementary holograms for the particulate element under consideration.

In this way, one understands that each resulting velocity hologram $H_N$ is obtained by temporal integration of successive elementary holograms $h_0$ to $h_N$ and that, for the medium ensemble, that is to say, for all the particulate elements contained in it, a spatial integration of the resulting velocity holograms into a composite velocity hologram allows for the final formation of the velocity holographic image at a given instant of illumination, which contains the mobility information of each of the particulate elements contained in the medium.

In particular, one can see in FIG. 3d, that the topography of each resulting velocity hologram $H_1$ to $H_N$ is modified by the aformentioned integration, each resulting velocity hologram, of a rank equal or greater than 1, consisting of a series of bands orthogonal to the direction of motion of the particulate element EP being considered.

In this way, it is indicated, particularly for the resulting velocity hologram $h_i$, that the bands formed on it, orthogonally to the direction of motion of the element EP, present, in the direction of motion, a dimension which is inversely proportional to the moving velocity of the particulate element EP in the aforementioned direction of motion. This law of the formation of bands is verified approximately for the resulting velocity holograms of higher rank, however, as represented in FIG. 3d, whenever the rank of those resultant velocity holograms grows, the holographic image obtained for these, is comprised of a series of graduated bands, each one comprised of approximately a portion of zone of the fringe pattern, the dimensions of these orthogonal bands signifying the particle's velocity parameters at prior instants of illumination.

A spatial Fourier transform, applied to each resulting velocity hologram allows one to retrieve, from the aforementioned bands, the velocity information of each particle being considered, which, in fact, allows for the decoding of the mobility information for each elementary particle EP, such as will eventually be described in the description.

A justification of the realization of the method for measuring the mobility distribution of distinctive mobile particulate elements in a medium, object of the present invention, will be given below.

The method for measuring the mobility distribution of mobile particulate elements, in a medium, can be justified from the relative fundamental elements of techniques of coherent or incoherent holography that will be recalled below.

In a general manner, it can be recalled that the coherent holography techniques consist of bringing the interference of two coherent light rays, that is to say in well-determined phase relation, an object beam and a reference beam.

More specifically, the coherent holography can be represented as the product of convolution of a three-dimensional distribution of an electric field, where the electric field of the electromagnetic wave consists of an illumination beam, and of a three-dimensional transfer function, in particular, that of each particulate element contained in the medium.

The function obtained from this convolution product is representative of the three-dimensional hologram obtained generally, that is to say, of the distribution in space of the light energy transmitted by the said transfer function.

The coherent hologram obeys equation (2) below:

$$H(x',y',z') = \int_V E(x,y,z) \exp\left( \frac{i\pi}{\lambda} \frac{(x-x')^2 + (y-y')^2}{(z-z')} \right)$$

In the preceding equation:

E(x, y, z) represents the electric field at point x,y,z, x',y',z' represent the coordinates in the Cartesian frame of a particulate point where the hologram is formed, x, y, z represent any coordinates of that spatial zone in this same Cartesian frame, $\lambda$ represents the wavelength of the object's illuminating beam, and, respectively, of the transmitted beam, and $j = \sqrt{-1}$.

To express the transfer function, one uses a signal representation in the form of a complex exponential function, which implies the expression of complex numbers in real values of amplitude and of phase. Also, in accordance with another convention admitted in holography, one part of the known signal is expressed in the form of continuous background, a measurable physical quantity, represented by the square intensity of the electric field. The convolution product given by the relation (2) can then be written in accordance with the relation (3) below:

$$H(x',y',z') = \int_V E(x,y) G[\alpha, x - x', y - y'] dxdydz.$$

As with many cases of coherent holography, the continuous background is not analyzed.

In the aforesaid relation (3), it is indicated that $G[\alpha, x-x', y-y']$ points to the transfer function of the hologram in a plane of dimension z', the $\alpha$ parameter being the parameter defined by the relation (4):

$$\alpha = \frac{\pi}{\lambda(z - z')}$$

An identical formalism has been developed by G. SIRAT (CONOSCOPIC HOLOGRAPHY: I-Basic Principles and Physical Basis; II-Rigorous Derivation. TELECOM PARIS 91C001, Fevrier 1991-Depot Legal, 1er. trimestre 1991- ISSN 0751 -1337) in the case of the conoscopic holography and it can be extended to the equivalent systems of incoherent holography or to interferometry by polarization. In accordance with that formalism, the preceding relations (2), (3), and (4) are obeyed by the relations (2'), (3'), and (4'), in which the electric field E(x, y, z) is replaced by the lighting intensity I(x, y, z), according to the relations:

relation (2')

$$H(x',y',z') = \int_V I(x,y,z) \exp\left[ j\pi K_0 \frac{(x-x')^2 + (y-y')^2}{(z_c - z')^2} \right] dxdydz$$

relation (3')

$$H(x',y',z') = \int_V I(x,y,z)G[\alpha, x - x', y - y']dx\,dy\,dz.$$

relation (4')

$$\alpha = \frac{\pi K_0}{(z_c - z')^2}$$

In those relations, $K_0$ is the conoscopic parameter defined in the document published by G. SIRAT, previously cited.

The longitudinal distances are replaced by the modified conoscopic longitudinal distances $Z_c$ according to the document published by G. SIRAT, in which the value is close to that of the longitudinal distance, within a close constant. For simplicity, the term of longitudinal distance, and the z symbol, will be used in the description below in place of the modified conoscopic longitudinal distance $Z_c$.

The parameter $\alpha$ in accordance with the relation (4') is an approximation to the Fresnel parameter $f_R$ as defined in the cited document of G. SIRAT.

In the same way as for conventional holography, the signal is represented by a complex exponential function.

Thus, it is understood that the elementary holograms used for implementation of the method aspect of the present invention, are embodied in a volume located in Cartesian coordinates by the directions x, y, z, each hologram comprising a fringe pattern or respectively a sinusoidal distribution of interference fringes. In this way, each elementary hologram is characterized by a parameter a, which, of course, is a function of the longitudinal position of the particulate element EP, that is to say, of the position in direction z.

In particular, it is to be noted that the said parameter a depends, in addition to the parameter of longitudinal position, parameter z or its extension in relation to an arbitrary value z', on the wavelength $\lambda$ of the lighting beam or of the transmitted beam. Parameter $\alpha$ is a parameter equivalent to the Fresnel parameter, such as defined in the case of a hologram obtained through conoscopic holography.

Taking into account the previous remark, it is indicated that whenever the illuminated object is approximately planar and chromatic, the wavelength of the transmitted beam, in this case of characteristics specific to the object, it is possible to characterize each resulting velocity hologram as a function of the wavelength or wavelengths comprising the lighting beam, and respectively the transmitted beam, and in this way of embodying the implementation of the method object of the present invention, not only with respect to approximately monochromatic light, but equally as well with respect to a light composed of an ensemble of approximately monochromatic rays.

This last property, in the case in which the thickness of the analyzed medium is relatively weak, permits the separation of different wavelengths, such as to discriminate among particles labeled by different fluorophores.

In this last case, each elementary hologram can, in fact, be comprised, for example, of a plurality of elementary holograms relative to each wavelength comprising the original composite light.

In the phenomenon of generalized holography, that is to say that in which the holographic phenomenon is embodied for a plurality of wavelengths constituting a composite light, it is possible to bring to the fore a parameter describing specific information relative to a particulate element and finally to the set of the particulate elements contained in the medium, that parameter being, such as corroborated through the inventor's studies, mathematically separable.

In this context, the term mathematically separable is to be understood in a weak sense, below described by the relation (5) and for which the function e is close to the impulse function $\delta$ in that it fulfills the following conditions:

$\epsilon_{\alpha\alpha'}=1$ for $\alpha=\alpha'$ $\epsilon_{\alpha\alpha'}$ is small, approaching 0, for $\alpha \neq \alpha'$.

One recalls that the function $\epsilon$ is of the form:

$$\epsilon = \frac{\sin(\alpha - \alpha')}{(\alpha - \alpha')} \text{ or } \epsilon = \left[\frac{\sin(\alpha - \alpha')}{(\alpha - \alpha')}\right]^2.$$

In such a case, the convolution product of the hologram in the x'y' plane can then be expressed the form of the relation (5) below:

$$\int_S G(\alpha, x', y')G(\alpha', x', y')\,dx'dy' = \epsilon_{\alpha\alpha'}.$$

In the preceding relation, it is indicated that the product of the convolution is obtained in this way, in a mathematically separable form of the product of a transfer function characterized by a distribution, denoted G(x, y), where x and y are the lateral position parameters, that is to say in a plane, that is to say the surface S over which the convolution product is done, and of a distribution G($\alpha$, x, y), which is characterized by the wavelength of the constituent rays of the composed light being utilized. In the preceding relation (5), $\alpha\alpha'$ designate the previously defined parameter in the relations (4) and (4').

In accordance with a particularly advantageous aspect of the method, object of the present invention, in certain cases, the medium can contain particulate elements labeled by fluorescent products eliciting a fluorescence at different wavelengths.

In this way, a chromatic object, that is to say a set of particulate elements which generate a transmitted beam composed of several rays or wavelengths, has the effect of generating a transfer function, which can be expressed, for the multiplicity of said wavelengths, in a mathematically separable form, such as previous! described. In a more precise fashion, whenever the transfer function is characterized by a distribution G($\alpha$, x, y), x and y being the lateral parameters of extension of each elementary hologram and $\alpha$ the parameter of those same holograms which depend of the longitudinal position, the mathematically separable expression of the convolution product allows, for example, to consider the use of chromatic particulate elements for two wavelengths $\lambda_1$ and $\lambda_2$ for which the modulation of transfer function by the auxiliary transfer function FTA can take distinctive values for said wavelengths $\lambda_1$ and $\lambda_2$. In this way, it is possible, in accordance with the method of the present invention, to separate, during the same procedure, the elementary holograms and the resulting velocity holograms relative to said wavelengths $\lambda_1$ and $\lambda_2$.

In terms of the real decoding of the resulting velocity holograms, it is indicated that several techniques can be used in order to achieve the decoding operation.

In a general way, in order to retrieve the velocity information from the resulting velocity holograms, it is indicated that the integration of the elementary holograms be performed, of course, with spatial-temporal reference. In this way, the specific discrimination for a particulate element EP can be performed by spatial discrimination of the maxima and the minima of correlation of each resulting velocity hologram taking it to a maximum of correlation coefficients with the position of the source particle.

For a given velocity, whenever the considered particulate element EP was excited at said velocity, the total of the light energy emitted by the considered and summed particulate element EP, which give rise to a maximum for the detected signal, that maximum being detected in an appropriate way, such as will be described below. Techniques of amplitude correlation with models of known amplitudes can then be used in order to perform this type of treatment.

In the specific case in which what is to be measured is the mobility parameter in only one lateral direction orthogonal to the said longitudinal direction, for example as for the sequencing of proteins or of labeled protein elements, or for sequences of these elements, the treatment can then be simplified in the particular way pointed out below.

In the case of the periodic sampling of the particulate movement in the aforementioned direction, the coded velocity information appears in the shape of an impulse function in the spatial domain. It is understood, in fact, that the successive bands orthogonal to the direction of motion of each particulate element EP bring with them the said coded information.

In such case, it is possible, in accordance with an advantageous aspect of the method implementation of the present invention, to apply a spatial Fourier transform on the obtained velocity hologram, then to perform a summation of the Fourier coefficients obtained in this way in the dimension perpendicular to the motion. In this way, the researched mobility information is obtained.

Other numerical techniques can be used in order to retrieve through decoding, the mobility information contained in the resulting velocity holograms.

Comparing with previous techniques, and particularly with the technique for getting the medium images by the rapid sequencing previously described in the description, it is indicated that, contrary to this previous technique, in which the mobility's spatial-temporal information pertaining to the mobility of the particulate elements is directly dependent on the temporal sequence of images, each resulting velocity hologram obtained through the implementation of the method in accordance with the invention, contains, in itself, the information on velocity or on mobility parameters for resulting velocity hologram was obtained.

Vis-a-vis the similarly described ETM method, in terms of prior art previously in the description, the method aspect of the present invention seems to be particularly advantageous in that it does not need any spatial separation of the particulate elements EP of different mobility.

For that reason, it is indicated that it is possible to obtain the sequencing velocities of proteins 3 to 8 times better than sequencing velocities of proteins as obtained by current classical methods.

Finally, it is equally notable that the optimization of choice of an optical marker, such as a fluorescent marker, for example, is not attached to the same criteria as in the case of the ETM method. According to the method aspect of the present invention, the choice of a marker depends on the average number of photons that a particle can emit before extinction of the temporal phenomenon or of the distinctive emission. This temporal or distinctive phenomenon is known under the name of Photo Bleaching or Photo Destruction in the corresponding technical domain.

In comparison with the prior art ETM, it is indicated that the parameter equivalent to the bandwidths D is, within the context of the implementation of the method aspect of the present invention, the creeping distance due to lack of the medium homogeneity for the dynamic behavior of each particulate element EP in that medium, and is, consequently, several orders of magnitude inferior to the usual width values of bands used in the precipitate ETM method.

In comparison with sequencing by the rapid images method, the method object of the present invention allows obtaining a comparable level of precision without the need for counting numerous photons, which, in fact, is practically unfeasible in many applications.

In comparison with the variant realization of this same technique of sequencing by rapid images, variant DPM, previously described in the description, it is indicated that the method aspect of the present invention avoids problems of ambiguity and, moreover, its measuring precision is superior to that of the DPM method.

A more detailed description of a device for measuring the mobility distribution of mobile particulate elements in a medium, in accordance with the method aspect of the present invention, will now be described in reference to FIG. 4 and the following figures.

Figure 4:
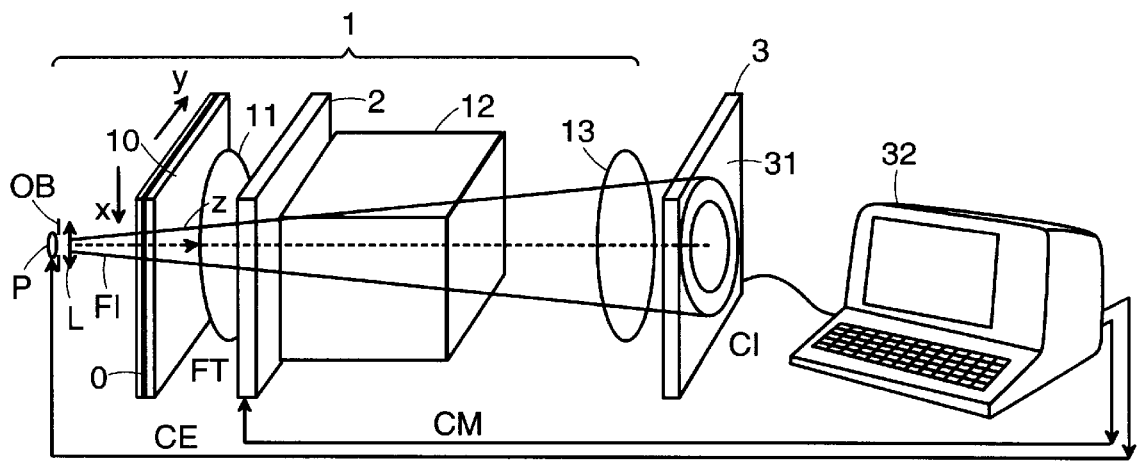
FIG. 4 represents, as an illustration, a device for measuring the mobility distribution of particulate elements, object of the present invention.

Such as can be noticed by looking at FIG. 4, it is indicated that the device aspect of the present invention comprises at least an incoherent holographic acquisition module 1 of a medium containing the particulate elements EP for which the mobility parameters are to be measured. In FIG. 4, the medium is denoted O, representing the object for analysis, for example, this object being represented as a laboratory preparation, where this preparation carries a section to be analyzed in the form of a gel, held between two sheets of transparent parallel faces.

Following convention, the directions x and y are contained in the plane of the section for analysis or in a plane perpendicular to a direction z, called an axial direction or an optical axis of the device. This axial direction is defined by the optical axis of the optical system positioned in front of the conoscope or of the interference system by polarization.

In the case in which the particulate elements EP are contained in a liquid, a resting, liquid or, if the case arises, a flowing liquid, the object O can be comprised of a reservoir which contains the liquid medium in which the particulate elements EP are present.

It is indicated that the holographic acquisition module 1, in incoherent holography, allows the formation, from a beam of illumination FI, for each of the particulate elements, an elementary hologram at periodically successive instants, such as previously described in the description about the implementation of the method in accordance with the invention.

As a non-limiting example, it is indicated that the acquisition module 1 comprises a source P equipped, for example, with a microscope optic, symbolized by a lens L in FIG. 4, where the module is comprised of the source P and the lens L supporting the reference 10.

The module 1 of incoherent holographic acquisition also has, in a first embodiment, a conoscope successively formed by a circular entry polarizer 11, a crystal 12, and a circular exit polarizer 13, these elements being aligned over the z axis represented in FIG. 4, to embody a conoscope which allows, from the transmitted beam FT by the object O. to form the elementary hologram for each particulate element EP present in the medium O.

For a more detailed description of a conoscopic device which constitutes said module 1, one can refer to U.S. Pat. No. 4,602,844.

In a general way, it is indicated that the polarizers, entry polarizer 11, and exit polarizer 13, are circular polarizers, and that the crystal 12 can, in fact, be comprised of an organization of two crystals, such as described in the cited U.S. patents.

As a non-limiting example, it is indicated that the types of crystal being used can, for example, be:

- a uniaxial crystal of which the crystalline axis is aligned over the longitudinal axis z of the ensemble, the uniaxial crystal being placed between two linear polarizers replacing the polarizers 11 and 13;
- a uniaxial crystal of which the crystalline axis is transverse to the system's longitudinal axis, the crystal being placed between two circular or linear polarizers;
- optically active crystals placed between circular or linear polarizers;
- a bi-axial crystal of which one of the crystalline axes is aligned along the system's longitudinal axis and placed between two linear polarizers;
- a bi-axial crystal not aligned over the system's longitudinal axis between two linear polarizers;
- two successively uni-axial crystals placed between linear or circular polarizers.

All the preceding transfer functions allow one to obtain results similar to those obtained through implementation of two-dimensional zoned patterns.

In addition, the use as transfer function FT of unidimensional zoned networks in order to embody an apparatus which allows the implementation of the method object of the present invention, can be considered as well.

When linear polarizers are used, it is indicated that the polarizers 11 and 13 can be embodied by Polaroid HN32 type of polarizers.

When circular polarizers are used, these can be embodied by a Polaroid HN32 linear polarizer on which a retardation plate is placed and glued over it. Such circular polarizer sets are embodied and commercialized in France by Societe FICHOU at 94260 Fresnes, France.

In terms of the excitation source P, it is noted that this can, for example, be embodied by a sodium source, this source being equipped, if the case arises, with a periodic shutter OB, electrically controlled.

In terms of the microscope objective L associated with the said source and to its shutter, it is indicated that this optic can be embodied by a microscope objective of magnification 10 and aperture 0,45. Said optic L defines the longitudinal axis or optical axis of the system, that is to say the axis z. Favorably, the optic L can achieve a lateral magnification $m_x$ in the direction x and a longitudinal magnification $m_z$ connected by the relation $m_z = m_x^2$.

In the case where the crystal 12 and the associated polarizing elements constitute a conoscope, it is indicated that the crystal 12 can be a calcite crystal, cleaved so as to align the crystal's crystalline axis with the system's optical axis, that is to say the longitudinal axis z. The mounting is nominally along the axis, and it presents a length that allows for the embodiment of a conoscopic figure, that is to say of a set of elementary holograms with dimensions, for example, between 2 and 30 mm. This configuration is embodied by conoscopic configuration along the axis.

Finally, it is indicated that an embodiment can equally consist of a calcite crystal which is cleaved so that its optical axis presents a slight inclination, for example of 2.5°, in relation to the optical axis of the system, the axis Oz.

These elements will not be described with great detail because they correspond to elements well known in this technology.

Furthermore, as represented in FIG. 4, the device aspect of the present invention is comprised of a modulation module 2 for modulating said transfer function by the specified auxiliary periodic transfer function FTA, the period of this transfer functions equal to or multiple of the period of the periodic successive instants of acquisition in order to allow for the labeling of each elementary hologram and, in this way, for generating, for each particulate element, of conjugated successive elementary holograms.

In a specific embodiment, it is indicated that modulation module 2 can be realized by a cell of nematic liquid crystals, which constitutes an electrically controlled retardation panel. When the electrically controllable retardation plate, is realized by a cell of nematic liquid crystals, this type of cell implements phenomena that are based upon the transmission of light by the liquid crystals, and this allows phase control of the electromagnetic wave constitutive of the luminous beam which go through the cell. In a non-limiting fashion, in order to realize a prototype of a device, such as represented, cells comprised of nematic liquid crystals, commercialized by Meadowlark Co., of Boulder, Colo., USA, were used.

Referring to modulation module 2, it is indicated that it can be placed anywhere between entry polarizer 11 and exit polarizer 13 constitutive of module 1 of incoherent hologram acquisition, with the condition of respecting the polarization laws as described in the French Patent No. 88 17225. Modulation module 2 can be place either upstream or downstream of crystal 12 placed between the polarizers.

Upstream from exit polarizer 13, as represented in FIG. 4, the device according to the invention provides an integrating module 3 which allows, at each instant of illumination or of formation of elementary holograms, to integrate the set of these holograms to form a resulting velocity hologram, this one containing the mobility information of each particulate element coded in this way.

In general, it is indicated that the integrating module 3 is favorably formed by a two-dimensional detector array, bearing numerical 31 in FIG. 4, in order to allow the generation, from each elementary hologram, of a numbered image consisting of a pattern of two-dimensional digital pixels. Integrating module 3 also provides a memory module 32 of digital pixels stored in many data files. Of course, the memory module 32 can be embodied by the memory elements of the dynamic memory type and/or mass memory of a microcomputer 32, which will be described in more detail further in the description. Each data file is representative of composite holograms, positive or negative, in relation to the set of particles integrated on the surface of the detector module 31 at one of the aforementioned periodic successive instants. The cited data files allow one to reconstitute, as previously mentioned in the description, on the one hand, the resulting velocity hologram such as previously described, $H_0$ to $H_N$, and, of course, the holographic images corresponding to the spatial-temporal integration of the said elementary holograms.

For the implementation of detector module 31 in the embodiment of a prototype of the device represented in FIG. 4, as a non-limiting example, an array camera was used, based upon the charge transfer effect CCD cooled by the Pelletier effect. This type of light detecting module is advantageous as long as the exit signal delivered by it is either analog or digital, of which a temporal sequence of data successively represents a signal proportional to the intensity detected by each pixel of the two-dimensional array.

Of course, in FIG. 4, the detecting module 31 is represented by a simple active surface so not to overload the drawing with the representation of a complete CCD camera.

Having accounted for the integrating functionalities of the aforementioned utilized CCD camera, it is, of course, understood that the spatial-temporal integration is performed directly through the pixels of the aforementioned camera, where the signal CI is then directly representative of the composed velocity hologram which 15 corresponds to a spatial integration of the resulting velocity holograms. These holographic images are then transmitted in the form of a corresponding electronic representation by the signal CI, as represented in FIG. 4, towards the microcomputer 32, which allows, if the need arises, for the transformation of this electronic representation into a digital representation for memorization in the form of the aforementioned data files and of subsequent treatment, so as to embody the mobility information decoding in conformity with the previously described method.

In terms of the functioning of the device represented in FIG. 4, it is indicated that the sequencing of the set of the constitutive elements of this device can be realized in the fashion discussed below, in reference to FIG. 3b in the case of a two -state of phase modulation such as previously described in the description.

The shutter OB is controlled by the sampling control signal CE, as represented in the aforementioned FIG. 3b. This allows for the illumination of the object O at successive illumination instants $t_i$ during the determined intervals $\Delta t$.

Of course, in a different non-limiting embodiment, it is indicated that the point source P can be permanently excited, and the shutter OB suppressed, while control signal CE is supplied to the CCD camera, that is to say to detecting module 31 represented in FIG. 4, in order to assure a periodic aperture of the camera's diaphragm and a periodic detection corresponding to the transmitted beam and the aforementioned holographic images at detection instants that, of course, turn into the aforementioned instants of illumination. It is understood that, while these two solutions are equivalent, their preferability depends on the application.

In particular, it is noted that for measuring mobility parameters of very mobile particles implying a very elevated sampling frequency, such as, for example, for mobility measurement of particles in liquids or in flowing gases, it will be preferable to control the source's shutters through a sampling signal CE. It is also understood that, in this case, the source can be realized through a coherent source controlled by impulse, this source being, for example, a ruby or another laser source.

Also, modulation module 2 receives modulation control signal CM delivered directly from microcomputer 32.

In the case such as the modulation represented in FIG. 3b, the modulation control signal CM is synchronized to the sampling signal CE. Modulation control signal CM allows, in this way, the modulation of the transfer function of the acquisition module 1 at the rhythm of modulation control signal CM.

Figure 5A:
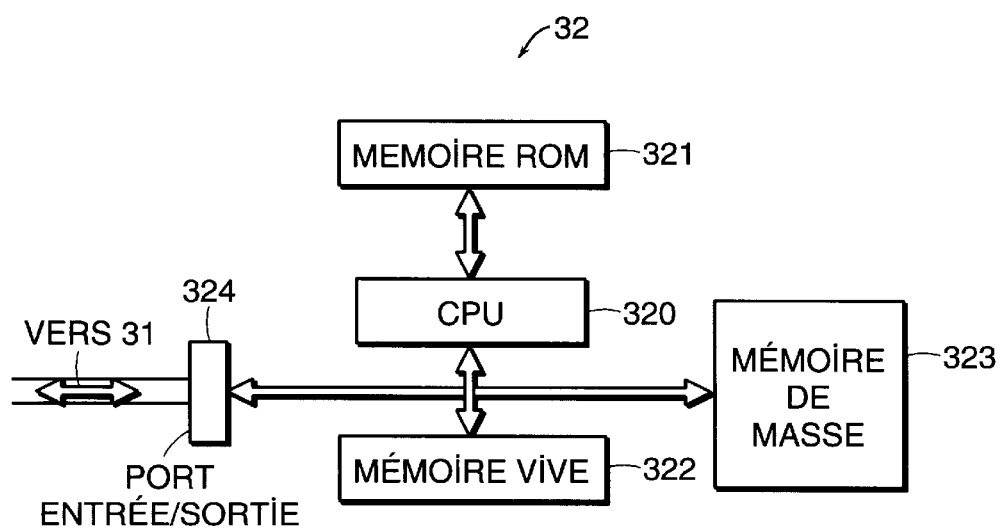
FIG. 5a represents, as an illustration, a detail of the embodiment of a decoding module of the resulting velocity holograms, by a micro-computer.

In order to realize the aforementioned functionalities, it is indicated that microcomputer 32 can, as represented in FIG. 5a, provide, in a classical way, a central processing unit 320, denoted CPU, a dynamic working memory 322, which allow the execution of programs for signal generation CE and CM and the reception of signals CI, constituting the data relative to the holographic images, and a mass memory 323 which allows the memorization of those data. A static memory type of memory 321 can be foreseen with the goal of allowing the implantation of programs dedicated to the decoding of the mobility information contained in the resulting velocity holograms and in the corresponding holographic images. The connection with detecting module 31 is realized in a classical way through an I/O port 324.

Figure 5B:
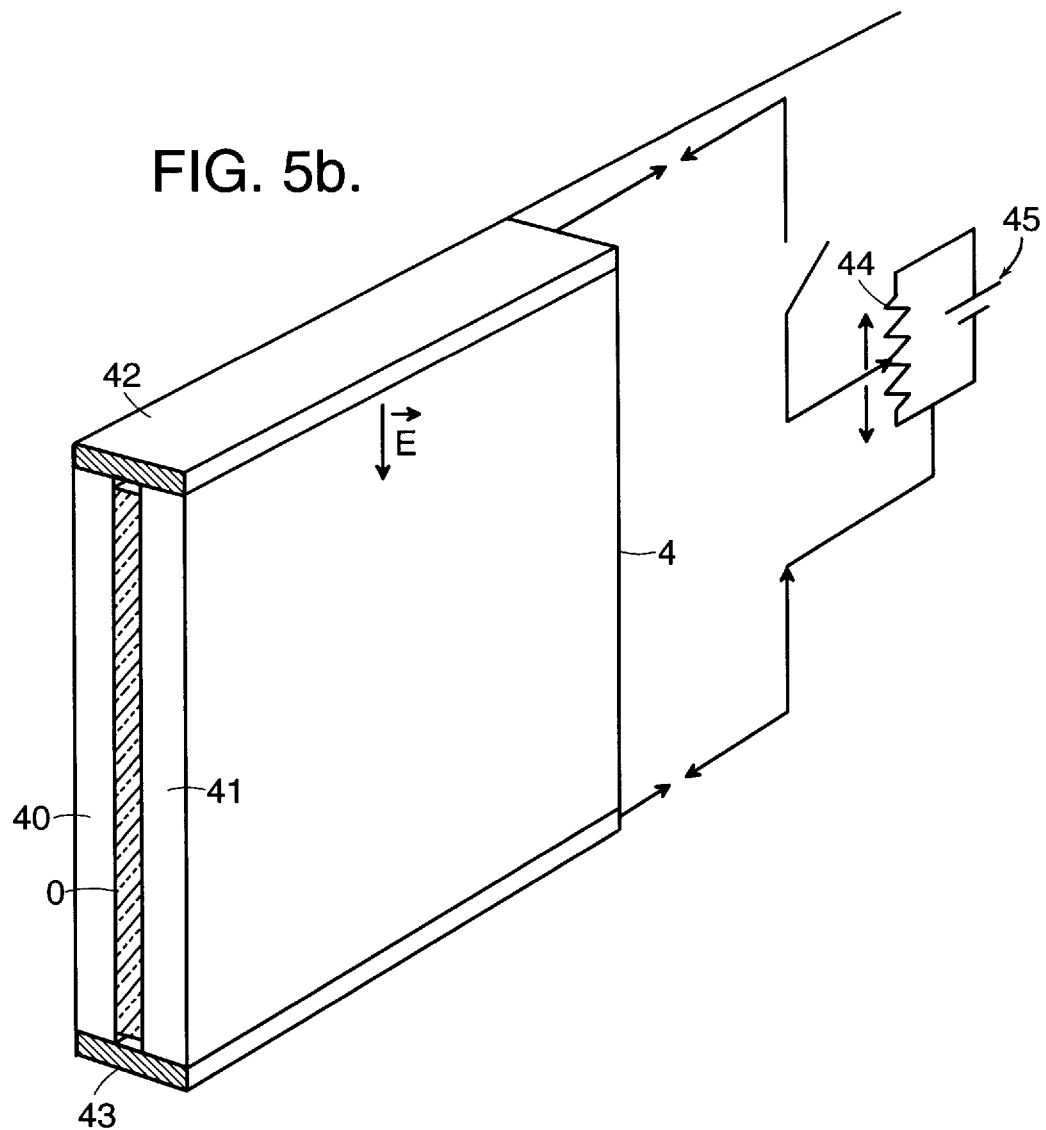
FIG. 5b represents a specific embodiment of an objective slide in the form of an electrophoresis cell, allowing the application of an external force which corresponds to a determined temporal law on the particulate elements.

An alternate embodiment of the device aspect of the present invention, equally allowing a variation of the embodiment of the method for measuring the mobility distribution of particulate elements previously described, will be presented in relation to FIG. 5b.

In accordance with a particularly favorable aspect of the method object of the present invention and of its embodiment, one can also apply an external force to the particulate elements EP to control their motion. The applied field of forces can be stationary or periodic to allow discrimination of the particulate elements EP as a function of their mechanical and/or dimensional features.

It is understood, in fact, that in the presence of a field of forces exerted on particulate elements EP, it is possible, under certain experimental conditions, to determine the mechanical parameters of the particulate elements.

In this way:

for an uniform field of forces, it is possible to determine mass information with respect to each particulate element EP, and for uniform masses, it is possible, in the presence of a field of forces, to determine instantaneous information with respect to forces being applied to the particulate elements of uniform mass.

In this last case, it is indicated that, in accordance with a particular embodiment of the method aspect of the present invention, it is advantageous to introduce into the medium witness particulate elements, of known calibrated mass, with the goal of determining the evolution of the forces applied to these elements in the course of their trajectory, in order to determine certain elements of interaction among particulate elements EP contained in that medium. This last embodiment is particularly advantageous for studying fields of forces in liquid or gas flows.

An important case for the application of such field of forces is that, when the particulate elements EP have inherent electric charge, instead of working with a preparation or a reservoir of liquid, such as previously described, to work with an electrosphoric cell, which holds electrodes 42 and 43, between two parallel facing transparent panels 40, 41, allowing the application of an electric field E oriented at a determined angle with respect to a direction of reference. An exciting electric potential can then be applied between the electrodes 42 and 43 with a voltage varying system as intermediary, 44,45, to apply a stationary or periodic electric field between the said electrodes. Under such conditions, the electrically charged particulate elements EP are subjected to an electrostatic type of force, which gives rise to the possibility of conducting the studies previously mentioned in relation to the mechanical or geometric figures of the aforementioned particulate elements.

A more detailed description of the procedure for decoding resulting velocity holograms obtained in accordance with the method aspect of the present invention, will now be provided in reference to FIGS. 5c and 5d.

In general, for a particulate element $EP_k$ of coordinates $x_k$, $y_k$, $z_k$, these coordinates representing, for example, the coordinates of this particulate element's center of gravity, with respect to an orthonormal coordinate system, such as represented in FIG. 4, and to that particulate element being associated a reference frame attached to the center of gravity in the directions x, y, z, previously mentioned for FIG. 4, one recalls the transfer function for the considered particular element given by relation (6):

$$\exp\left[j\pi K_0 \frac{x_k^2 + y_k^2}{z_k^2}\right].$$

For a considered particulate element $EP_k$, driven with a velocity of which the components that follow the line in the directions x, y, z of FIG. 4 are: $W_x$, 0, $W_z$, being presumed so to simplify the statement that each particulate element is driven with a motion in the xz plane, for example, the transfer function of the device, as represented in FIG. 4, that is to say, at the time when a modulation as a function of the time of that transfer function with a frequency $f_m$ with $\omega = 2\pi \cdot f_m$, satisfies the relation (7) below:

$$G(x',y',z') = \int_{-T}^{T} \exp\left[j\pi K_0 \frac{(x_k - x' + W_x t)^2 + (y_k - y')^2}{(z_k - z' + W_z t)^2}\right] \exp[j\omega t] dt$$

The said transfer function is given as a function of coordinates x', y', and z', of hologram $x_k$, $y_k$, and $z_k$ of the Cartesian frame associated with the center of gravity of the particulate element $EP_k$.

The aforementioned relation (7) corresponds to a sampled transfer function for which the contribution of each particulate element $EP_k$ is calculated for a sampling duration tending towards an infinite value.

In the following description, the simplifying hypothesis is formulated, in accordance with which $W_z=0$, $W_x$ being denoted $V_k$. Similarly, according to a convention admitted for signal theory, the calculation of a spatial Fourier transform is performed in the case of an infinite temporal integration $T \to \infty$.

A spatial Fourier transform applied to the said transfer function allows one to obtain the expression for the corresponding lighting distribution, on a plane orthogonal to direction z, and extending in the directions x', y', in plane z'=0 and corresponding to the plane which contains the previously described bidimensional detector array 31. This plane will be designated in terms of coordinates $\nu$ and $\mu$, $\nu$ being the conjugate of direction x and $\mu$ the conjugate of direction y.

The expression of the said Fourier transform, then, provides the spatial frequency of the lighting pattern, that is to say, of the intensity, in the plane of the aforementioned directions x, and y, and satisfies the expression (8):

$$G'(\nu,\mu) = \exp[j2\pi(\nu x_k + \mu y_k)] \int_{-\infty}^{\infty} \frac{-j}{K_0} \exp[j2\pi\nu V_k t] \exp\left[\frac{jz_k^2 \rho^2}{K_0}\right] \exp[j\omega t] dt$$

with $\rho^2 = (\nu^2 + \mu^2)$.

Notation G' designates the aforementioned expression for the spatial Fourier transform, obtained from the preceding transfer function.

The regrouping of the terms, as a function of time t, allows for the new expression that satisfies relation (9):

$$G'(\nu,\mu) = \frac{-j}{K_0} \exp[j2\pi(\nu x_k + \mu y_k)] \exp\left[j\frac{\pi z_k^2 \rho^2}{K_0}\right] \delta(2\pi\nu V_k + \omega)$$

with $$\delta(2\pi\nu V_k + \omega) = \int_{-\infty}^{\infty} \exp[j(2\pi\nu V_k + \omega)t] dt \text{ and } j = \sqrt{-1},$$

$\delta$ representing the impulse function.

Therefore, in the Fourier domain, that is to say, in the plane of the bidimensional detector array 31, one obtains lines perpendicular to the direction of propagation to a position which is inversely proportional to the velocity of the particulate element $EP_k$ being considered.

Taking into account this explanation, the decoding procedure consists, in a non-limiting fashion, as represented in FIG. 5c, of calculating, in a step 200, all the resulting velocity holograms, from the information provided by the detector module 31 and from an ordering sub-routine, intensity information as provided by each pixel in the form of a bidimensional matrix that satisfies relation (10):

$$A(i,l) = CI\left(\frac{x}{\Delta x}, \frac{y}{\Delta y}\right)$$

i and l representing the pixel addresses.

In this relation, it is indicated that the corresponding values are, of course, a function of the position of each pixel and of the spacing between the said pixels. Parameter C is a parameter of intensity scale and of sensitivity of the detector module 31.

The said step 200 is followed by the actual calculation step for the spatial Fourier transform, denoted 201, where this step is realized for a M×M pixel matrix corresponding to the number of pixels of the camera being used. Step 201 can be realized through a specific program, based upon Cooley-Tukey's fast Fourier transform algorithm. Step 201 allows for the realization of the operation that provides the bidimensional spatial transform of the preceding transfer function G, described in the description by relations (7) to (9).

This operation allows one to obtain the spatial Fourier transform that satisfies relation (11):

$$a(\nu,\mu) = \sum_{0}^{M-1} \sum_{0}^{M-1} A(i,l) \exp[2j\pi(i\nu + l\mu)/M]$$

The preceding expression can be expressed, in a step 202, in the form of relation (12) below:

$$a(\nu,\mu) = -\frac{j}{K_0} \exp[2j\pi(\nu x_k + \mu y_k)] \sum_k \exp\left[j\frac{2\pi z_k^2 \rho_k^2}{K_0}\right] \cdot \delta(2\pi\nu V_k + \omega)$$

The said relation (12) allows one, thus, to determine the mobility parameters from measurement of the spatial frequency parameters $\nu$, $\mu$ and from the global expression as a function of the velocity of the considered particulate element $EP_k$, denoted $V_k$.

A more detailed description of the determination of the mobility parameter, of a class of the said particulate elements being considered, will now be provided in reference to FIG. 5d, for the case in which the drift direction is approximately parallel to one of the axes of the detector array, for example, direction x.

In such a case, it is indicated that the projection along an axis which is perpendicular to the drift direction in the plane being considered, that is to say, following the y axis, corresponds to the summation algebraic or not, of elements of the representative matrix of the spatial Fourier transform $a(v, \mu)$ calculated along the y axis.

As represented in FIG. 5b, the decoding procedure consists, in a step 2020, of performing such a summation in the said y direction, that is to say, for a pixel step with $v$ varying from 0 to M-1, with the spatial Fourier transform $a(v, \mu)$ being associated with some algebraic relation F. Preferably, relation F is the identity relation.

Step 2020 is followed by step 2021 in which, through an inversion of the summation order, the spatial Fourier transform relation, reduced on the perpendicular direction y in accordance with relation (13):

$$A(v) = \frac{-j}{K_0} \sum_k \delta(2\pi v V_k + \omega) \cdot E_k$$

with $$E_k = \exp[2j\pi(vx_k + \mu y_k)] \sum_{\mu=0}^{M-1} \exp j \frac{\pi z_k^2 \rho_k^2}{K_0},$$

in which relation $E_k$ represents the contribution of the particulate element $EP_k$. Finally, a step 2022 allows for the expression of the said relation (13), in the form of a velocity law, satisfying relation (14):

$$b(v) = + \frac{-j}{K_0} \sum_{v=v_k} E_k$$

in which, for a velocity value v, the contribution of the distribution of spatial intensity in the direction orthogonal to the drift direction, that is to say, to expression b(v), results only from particles that have the $V_k = v$ property. A separation as a function of the velocity contributions of different particles can then be achieved.

A more detailed description of a specific way for implementing the method and the device, objects of the present invention, particularly as previously represented in FIG. 4, in the case where the beam of illumination FT and the transmitted beam FT are comprised of two rays of distinct wavelengths $\lambda_1$ and $\lambda_2$, will now be provided with referrence to FIGS. 6a, 6b, and 6c. The discrimination procedure is described for two wavelengths, but it can be also generalized for three or more wavelengths, by 5 introducing correspondingly distinctive dephasings, 0, $\pi/2$, $\pi$ either by separation through filters into several chromatic channels, or by using, such as previously described, a separation by generalized holography, or by using a combination of both of the above.

In FIG. 6a, the device previously represented in FIG. 4 is represented, in a 10 particularly advantageous embodiment, in which the entry-exit polarizers 11, 13 previously constituted either by absorption polarizer, or by angular separation polarizers, such as the so-called Wolaston polarizers, are, for example, replaced by spatial separation polarizers, such as the so-called Rochon polarizers, or by polarizing separators, in which the two polarizations are laterally spatially separated. In FIG. 6a, the entry-exit polarizers carry the reference 110, 130, and are comprised of absorption polarizers.

In a particular embodiment, it is indicated that when one of the polarizers, the entry polarizer, is comprised of a Rochon polarizer, the other one, the exit polarizer, is, for example, constituted by an absorption polarizer or, reciprocally, it is possible to obtain two spatially graduated complementary holograms. For a more detailed description of a corresponding embodiment, it is possible to look in the French Patent No. 88-17225, or French Patent No. 91-14661 which presents a device based upon a similar principle.

The aforementioned mode of implementation allows, by algebraically subtracting the corresponding positive and negative elementary holograms, to subtract the continuous background superposed on the hologram, and to obtain, in this way, a clean signal. Consequently, the use of only one Rochon polarizer, either at the entry or at the exit, allows one to obtain a differential signal.

In accordance with the preferred embodiment of FIG. 6a, it is indicated that the entry-exit polarizers 110, 130, each being composed of a Rochon polarizer, the entry polarizer 110 allows one to obtain the two holograms over two separated detectors.

The exit polarizer 130, equally composed of a Rochon polarizer or of a polarizing separator, is arranged in such a way that it allows one to obtain two holograms at separated detectors.

As represented in FIG. 6b, one obtains, in this manner, four elementary holograms, respectively denoted $h_{is+}$, $h_{is-}$, $h_{ie+}$, $h_{ie-}$.

The elementary holograms are matched pair by pair, two holograms being positive, namely, the elementary holograms $h_{is\ +}$ and $h_{ie\ +}$, and two elementary holograms being negative, $h_{is-}$ and $h_{ie-}$.

In this way, it is possible to reconstitute an elementary hologram, which, analogously to the method previously described, is denoted $h_i$ and satisfies relation (15):

$$h_i = (h_{is+} + h_{ie+}) - (h_{is-} + h_{ie-}).$$

The reconstituted hologram corresponds, therefore, to the difference between the sum of the two positive elementary holograms and the sum of the two negative elementary holograms. Such a solution is, at the energy level, completely satisfactory as long as none of the photons is lost during the implementation of the procedure.

In addition, the aforementioned embodiment allows, as well, to separate two wavelengths $\lambda_1$ and $\lambda_2$, which are constitutive of the transmitted beam FT. In effect, in such a case, a supplementary element is added to the modulation module 2, such as would correspond to a half-wave plate for wavelength $\lambda_1$, whereas the modulation module 2 constitutes a whole-wave plate for the second wavelength $\lambda_2$.

In such a case, the dephasings brought about for the two components $\lambda_1$ and $\lambda_2$, are presented in the Table represented in FIG. 6c.

In such an embodiment, the positive and the negative elementary holograms are inverted for the first wavelength, for example wavelength $\lambda_1$, and, respectively for the second wavelength $\lambda_2$ with:

first commutation $\lambda_1$:

$$h_{is-} = -h_{is+} \text{ and } h_{es-} = h_{ie+}$$

$$h_i = 2h_{is+}.$$

second commutation $\lambda_2$:

$$h_{is-} = h_{is+} \text{ and } h_{es-} = -h_{ie+}$$

$$h_i = 2h_{ie+}.$$

In such a case, the reconstituted elementary hologram $h_i$ corresponds to a hologram at the first wavelength $\lambda_1$, and respectively to the hologram of the second wavelength $\lambda_2$ as a function of the commutation realized in accordance with the diagram in FIG. 6c. In this way, one obtains a separation of holograms of wavelengths $\lambda_1$ and $\lambda_2$, which are components of the illuminating beam or the transmitted beam. For a practical implementation of the embodiment as described in FIGS. 6a and 6b, one can use a panel commercialized by Societe FICHOU at 94260 Fresnes, France, previously mentioned in the description.

Finally, the method and the device aspects of the present invention, are to be noted for the fact that they allow one to discriminate particulate elements with different spectral distributions and, thus, labeled by different fluorophores.

I claim:

1. A method of measuring the mobility distribution of distinct mobile particulate elements in a medium by means of incoherent light holography, said particulate elements being optically labeled, the method comprising:

forming, for each particulate element, an elementary hologram at periodic successive instants, each elementary hologram being representative at said instants of a transfer function of said particulate element in said medium, and being a function of the instantaneous position of said particulate element;

modulating said transfer function by means of a specified periodic transfer function having a period equal to or a multiple of the period of periodically successive instants, for labeling each elementary hologram and for generating for each particulate element, successive conjugate elementary holograms, corresponding to transfer functions shifted with respect to the modulation value of the specified transfer function;

integrating, at each instant of the formation of the elementary holograms, the ensemble of said conjugate elementary holograms, for forming a composite velocity hologram, containing mobility information of each particulate element encoded in that manner;

decoding each composite velocity hologram for obtaining the mobility information of one or several particulate elements.

2. A method in accordance with claim 1, wherein the step of forming, for each particulate element, an elementary hologram, includes illuminating said medium, containing the particulate elements, either to form ordinary or extraordinary beams generated in incoherent light by means of a conoscope, each elementary hologram consisting of a holographic image of a zoned network type, or to form the direct and retarded beams in incoherent light at least through a bi-refringent crystal, each elementary hologram consisting of a holographic image of sinusoidal intensity law.

3. A method in accordance with claim 2, wherein the step of modulating the transfer function by means of a specified periodic transfer function, comprises:

introducing an auxiliary transfer function onto the trajectory of the illumination beam transmitted by the aforesaid medium; and periodically commuting this auxiliary transfer function between a first and a second value, for shifting the transfer function, associated with each particulate element by a corresponding value, and generating, for two successive elementary holograms, related to a same elementary particle, complementary holographic images.

4. A method in accordance with claim 2, wherein the step of modulating the transfer function by a specified periodic transfer function includes:

introducing an auxiliary transfer function onto the trajectory of the transmitted beam, said auxiliary transfer function being continuously variable in time;

controlling the time variation of the auxiliary transfer function, in accordance with a series of periodic auxiliary transfer function values, for shifting the transfer function associated with each particulate element by a corresponding modulation value, and for generating conjugate holographic images for two successive elementary holograms, related to a same elementary particle.

5. A method in accordance with claim 1, further comprising the step of applying to the particulate elements, one of a periodic external force field and a stationary external force field, for discriminating said particulate elements as a function of at least one of their mechanical and dimensional characteristics.

6. A method in accordance with claim 1, wherein the elementary holograms are generated in approximately monochromatic light.

7. A method in accordance with claim 1, wherein the elementary holograms are generated for a plurality of substantially monochromatic lights of distinct wavelengths.

8. A device for measuring the mobility distribution of distinct mobile particulate elements in a medium, said particulate elements being optically labeled, the device comprising:

means for incoherent holographic acquisition of the medium and of each particulate element, such as to form an elementary hologram at periodically successive instants, from an illumination beam having a trajectory corresponding to each particulate element, each elementary hologram being representative at those instants, of the transfer function of said particulate element in said medium, and a function of the instantaneous position of that particulate element;

means for modulating said transfer function by a specified periodic transfer function, the period being equal to or a multiple of the period of periodically successive instants, such as to label each elementary hologram and to generate for each particulate element, successive conjugate elementary holograms, corresponding to transfer functions shifted from the modulation value of the specified transfer function;

integrating means for integrating, at each instant of the formation of elementary holograms, the ensemble of these elementary holograms, such as to form a composite velocity hologram, containing the mobility information of each particulate element coded in this manner; and means for decoding each composite velocity hologram, in order to obtain the mobility information of one or several particulate elements.

9. A device in accordance with claim 8, wherein the means of incoherent holographic acquisition includes:

means for generating, for each particulate element, elementary holograms; and means for commuting the generating means, at periodic instants, for generating the aforesaid elementary holograms at those instants.

10. A device in accordance with claim 8, wherein the modulation means comprises:

an optical valve, having at least two states of transmission, disposed along a trajectory of a transmitted beam, each transmission state corresponding to a value determined as a function of a specified periodic transfer function; and means for commutation of the optical valve from one to the other transmission state, at instants in which the period is equal to or a multiple of the period of periodically successive instants.

11. A device in accordance with claim 8, wherein the aforesaid integrating means comprises:

bidimensional detector array means for engendering from each elementary hologram a numbered image consisting of a network of bidimensional numerical pixels; and memory means for storing the numerical pixels in a plurality of data files, each data file being representative of the composite velocity hologram.

12. A device in accordance with claim 8, wherein said decoding means includes:

calculating means provided with a dynamic memory and with a programmable static memory; and a decoding program, written in the programmable static memory, for establishing the mobility parameters of at least one particulate element, starting from each data file or from a part of a data file loaded in the dynamic memory.

13. A device in accordance with claim 8, further comprising:

means for applying to each particulate element a periodic or stationary external field of force, for discriminating said particulate elements as a function of at least one of their mechanical and dimensional characteristics.

14. A device in accordance with claim 13, wherein the applying means includes an electrophoretic cell, having two transparent parallel faces, the medium containing the particulate elements introduced into said electrophoretic cell, said electrophoretic cell disposed along the trajectory of said illumination beam.

15. A device in accordance with claim 8, wherein the holographic acquisition means include a conoscopic device coupled to the illuminating beam, the conoscopic device having entry and exit polarizers each formed of a Rochon polarizer or a polarizing separator, and wherein the modulation means are formed of a half-wave, whole wave panel and whole wave, half-wave at a first and a second wavelength $\lambda_1$ and $\lambda_2$ respectively, such as to separate, through selective control, the elementary holograms of wavelengths $\lambda_1$, and $\lambda_2$ of the components of the transmitted beam of illumination.

* * * * *

UNITED STATES PATENT AND TRADEMARK OFFICE
CERTIFICATE OF CORRECTION

PATENT NO. : 5,892,602
DATED : April 6, 1999
INVENTOR(S) : Gabriel Y. Sirat

It is certified that error appears in the above-identified patent and that said Letters Patent is hereby corrected as shown below:

On the title page, Item [73],
In the Assignee change "Optiment, Optical Metrology Ltd." to --Optimet, Optical Metrology Ltd.-
Col. 26, ln. 12, change "include" to --includes--.

Signed and Sealed this

Third Day of August, 1999

Attest:

Attesting Officer

Q. TODD DICKINSON

Acting Commissioner of Patents and Trademarks